(12) United States Patent
Aggarwal et al.

(10) Patent No.: US 10,477,788 B2
(45) Date of Patent: Nov. 19, 2019

(54) METHODS AND COMPOSITIONS FOR IDENTIFYING VERTICILLIUM WILT RESISTANT SUNFLOWER PLANTS

(71) Applicant: Agrigenetics, Inc., Indianapolis, IN (US)

(72) Inventors: Rajat Aggarwal, Zionsville, IN (US); Martin Ariel Cantore, Buenos Aires (AR); Natalia Mercedes Paz, Santa Fe (AR)

(73) Assignee: Agrigenetics, Inc., Indianapolis, IN (US)

(*) Notice: Subject to any disclaimer, the term of this patent is extended or adjusted under 35 U.S.C. 154(b) by 0 days.

(21) Appl. No.: 14/946,366

(22) Filed: Nov. 19, 2015

(65) Prior Publication Data

US 2016/0150747 A1    Jun. 2, 2016

Related U.S. Application Data

(60) Provisional application No. 62/085,841, filed on Dec. 1, 2014.

(51) Int. Cl.
*A01H 1/04* (2006.01)
*C12Q 1/6895* (2018.01)

(52) U.S. Cl.
CPC ............. *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

Alves (Int. J. Mol. Sci. (2013), 14, pp. 7815-7828).*
Lai et al. (Theor. Appl. Genet. (2005), 111: pp. 1532-1544).*
Galella (In: Proc. 16th Int. Sunfl. Conf. Argentine, Mar del Plata (2012), pp. 1-6).*
Radi and Gulya 2006 Sources of Resistance to a New Strain of Verticillium dahliae on Sunflower in North America (Year: 2007).*
Acciarri, et al, Molecular markers for Ve1 and Ve2 Verticillium resistance genes from Italian tomato germplasm, Plant Breeding 126, 617-621(2007).
Sadras et al, Effect of Verticillium dahliae on Photosynthesis, Leaf Expansion and Senescence of Field-grown Sunflower, Annals of Botany, 86: 1007-1015 (2000).
Bolek et al., Mapping of verticillium wilt resistance genes in cotton, Plant Science 168: 1581-1590 (2005).
Collins, et al, Correlation of molecular markers and biological properties in Verticillium dahliae and the possible origins of some isolates, Plant Pathology 54: 549-557 (2005).
Creus, et al., Disease Expression an dEcophysiological Yield Components in Sunflower Isohybrids with and without Verticillium dahliae Resistance, Crop Science 47: 703-710 ((Mar.-Apr. 2007).
Diwan et al, Mapping of Ve in tomato: a gene conferring resistance to the broad-spectrum pathogen, Verticillium dahliae race 1, Theory Applied Genetics, 98: 315-319, (1999).
Fradin, Genetic Dissection of Verticillium Wilt Resistance Mediated by Tomato Ve11[c][w][oa], Plant Physiology 150:320-332 (2009).
Garcia-Cameros, et al, Genetic and Molecular Approach to Verticillium dahliae Infecting Sunflower, Helia 37(61): 205-214 (2014).
Galena, et al., Pyramiding QTLs for Verticillium dahliae resistance, Proc. 18th Int. Sunf. Conf. Mar del Plata & Balcarce, Argentina, pp. 219-224 (2012).
Yang, et al, QTLs mapping for Verticillium wilt resistance at seedling and maturity stages in *Gossypium barbadense* L., Plant Science 174, 290-298 (2008).

* cited by examiner

*Primary Examiner* — Brent T Page

(57) ABSTRACT

The present invention relates to methods for identifying sunflower lines having increased resistance to *Verticillium* wilt, and identification of genetic markers linked to gene(s) conditioning such increased disease resistance. The present invention also relates to methods of breeding sunflower plants from lines having increased *Verticillium* wilt resistance by marker-assisted selection, compositions including nucleic acid probes or primers which are useful for such marker assisted selection, and plants and plant parts produced by such methods.

2 Claims, 3 Drawing Sheets

Specification includes a Sequence Listing.

METHODS AND COMPOSITIONS FOR IDENTIFYING VERTICILLIUM WILT RESISTANT SUNFLOWER PLANTS

CROSS REFERENCE TO RELATED APPLICATIONS

This Application claims priority from, and benefit of, U.S. Provisional Application 62/085,841 filed on Dec. 1, 2014. The entire contents of this application are hereby incorporated by reference into this Application

INCORPORATION OF SEQUENCE LISTING

The sequence listing that is contained in the file named "70699-US-PSP-20141201-ST25.txt", which is 6000 bytes (measured in MS-WINDOWS), created on Dec. 1, 2014 is filed herewith by electronic submission and is incorporated herein by reference.

FIELD OF THE INVENTION

The invention relates to methods and compositions for identifying and breeding of sunflower plants having *Verticillium* wilt resistance.

BACKGROUND OF THE INVENTION

Sunflower (*Helianthus annuus*) is an annual plant, native to the Americans, that is cultivated for use as a confectionary seed as well as for production of cooking oil. Sunflower is an important agricultural crop in the northern plains of the United States from the Dakotas to the panhandle of Texas, throughout Canada, Argentina, and in Russia, Ukraine, and other European countries.

*Verticillium* wilt is caused by one of three species of *Verticillium* fungus, *V. dahlia, V. alboatrum,* or *V. longisporum*, which cause significant crop losses among many eudicot plants, including cotton, tomatoes, potatoes, eggplants, peppers, ornamentals, and sunflowers. Monocots, gymnosperms and ferns are immune. Symptoms are superficially similar to *Fusarium* wilts. Wilt itself is the most common symptom, with wilting of the stem and leaves occurring due to the blockage of the xylem vascular tissues and therefore reduced water and nutrient flow. In small plants and seedlings, *Verticillium* can quickly kill the plant while in larger, more developed plants the severity can vary. Sometimes only one side of the plant will appear infected because once in the vascular tissues, the disease migrates mostly upward and not as much radially in the stem. (Pegg, G. F., Brady, B. L. (2002) *Verticillium* Wilts, CABI Publishing, New York, N.Y.). Other symptoms include stunting, chlorosis or yellowing of the leaves, necrosis or tissue death, and defoliation. Internal vascular tissue discoloration might be visible when the stem is cut. No chemical control for the disease is available, but the use of crop rotation and resistant varieties, along with deep plowing, have been found useful in reducing the spread and impact of the disease.

Besides being long lasting in the soil, *Verticillium* can spread in many ways. The most common way of spreading short distances is through root to root contact within the soil. Roots in natural conditions often have small damage or openings in them that are easily colonized by *Verticillium* from an infected root nearby. Air borne conidia have been detected and some colonies observed, but mostly the conidia have difficulty developing above ground on healthy plants. (Easton, G. D., Nagle, M. E. and Bailey, D. L. (1969) A method of estimating *Verticillium* propagules in field soil and irrigation waste water. *Phytopathology* 59, 1171-1172.) In open channel irrigation, *V. dahliae* have been found in the irrigation ditches up to a mile from the infected crop. *Verticillium* wilt begins as a mild, local infection, which over a few years will grow in strength as more virile strains of the fungus develop. If left unchecked the disease will become so widespread that the crop will need to be replaced with resistant varieties or planted with a new crop altogether. (Agrios, George N., Plant Pathology, 5th Edition).

Control of *Verticillium* can be achieved by planting disease free plants in uncontaminated soil, planting resistant varieties, and refraining from planting susceptible crops in areas that have been used repeatedly for solanaceous crops. Soil fumigation can also be used, but is generally too expensive over large areas.

In tomato plants the presence of ethylene during the initial stages of infection inhibits disease development, while in later stages of disease development the same hormone will cause greater wilt. Tomato plants are available that have been engineered with resistant genes that will tolerate the fungus in their system, while showing significantly lower signs of wilting.

*Verticillium albo-altrum, Verticilium dahliae* and *V. longisporum* can overwinter as melanized mycelium or microsclerotia within live vegetation or plant debris. As a result it can be important to clear plant debris to lower the spread of disease. *Verticillium dahliae* and *V. longisporum* are able to survive as microsclerotia in soil up to 15 years.

*Verticillium* Wilt caused by the soil borne fungus *Verticillium dahliae*, is one of the most significant diseases in Argentina and is a growing problem in the United States. One of the major control strategies for this disease is to plant resistant varieties. A single dominant gene is believed to control *Verticillium* wilt resistance in sunflower (Fick and Zimmer 1974).

BRIEF SUMMARY OF THE INVENTION

The current study was undertaken to map quantitative trait loci (QTL) associated with *Verticillium* wilt resistance. An F4 mapping population of 260 individuals segregating for *Verticillium* wilt resistance was created from the cross of CN8861R (resistant source) and ONN120R (susceptible source). 188 polymorphic SNP markers were used to map *Verticillium* wilt resistance QTL. A single major QTL was identified on chromosome 10, explaining 65% of the variation. The QTL interval is flanked by single nucleotide polymorphism (SNP) markers DHAI005760 and DHAI006271.

In a first aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker and the QTL that confers resistance to *Verticillium* wilt; wherein the QTL maps to a position between the sequence represented by SNP markers DHAG001 106 and DHAI006271 which map to approximately 0 cM and 54.7 cM on the genetic map of the sunflower chromosome 10.

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker and the QTL that confers resistance to *Verticillium* wilt; wherein the major QTL maps to a position between the sequence represented by SNP markers DHAI005760 and DHAI006271 which map to approximately 46.5 cM and 54.7 cM (approximately 8.2 cM apart) on the genetic map of sunflower chromosome 10.

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker and the QTL that confers resistance to *Verticillium* wilt; wherein the major QTL maps to a position between the sequence represented by SNP markers DHAI000041 and DHAI006271 which map to approximately 47.2 cM and 54.7 cM (approximately 7.5 cM apart) on the genetic map of sunflower chromosome 10.

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker and the QTL that confers resistance to *Verticillium* wilt; wherein the QTL maps to a position between the sequence represented by SNP markers DHAG001 106 and DHAI006271 which map to approximately 0 cM and 54.7 cM (approximately 54.7cM apart) on the genetic map of sunflower chromosome 10.

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker that confers resistance to *Verticillium* wilt; wherein the minor QTL maps to a position near the sequence represented by SNP marker DHAG000460 on the genetic map of sunflower chromosome 10, where the minor QTL here has a negative additive effect (in this instance, deriving from the susceptible parent, not the donor parent).

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker that confers resistance to *Verticillium* wilt; wherein the minor QTL maps to a position near the sequence represented by SNP marker DHAI007648 on the genetic map of sunflower chromosome 11.

In particular embodiments, the QTL allele which confers resistance to *Verticillium* wilt is derived from sunflower line Paraiso 20, or a progeny plant thereof. In other embodiments, the QTL allele which confers resistance to *Verticillium* wilt is derived from sunflower line CN8861R, or a progeny plant thereof.

In certain embodiments, the genetic marker is selected from the group consisting of markers DHAG001 106, DHAI006271, DHAI000041, DHAI005760, DHAG000460, and, DHAG000083, DHAI007648. Further, in such embodiments assaying the sunflower plants comprises PCR, single strand conformational polymorphism analysis, denaturing gradient gel electrophoresis, cleavage fragment length polymorphism analysis, TAQMAN assay, and/or DNA sequencing. Further, in certain embodiments the genetic marker may map within 20 cM, 10 cM, 9 cM, 8 cM, 7 cM, 6 cM 5 cM, 4 cM, 3 cM, 2 cM, or 1 cM of a QTL which confers resistance to *Verticillium* wilt.

In some embodiments the sunflower plant comprising at least one allele which confers resistance to *Verticillium* wilt demonstrates a reduction of wilt of at least, or greater than, 25%, relative to a non-resistant control sunflower line.

In another aspect, the invention provides an isolated nucleic acid probe that hybridizes under conditions of 5×SSC, 50% formamide, and 42° C. to a sunflower plant genomic region mapping within 40 cM of a QTL which confers resistance to *Verticillium* wilt and comprises a sequence which maps on sunflower chromosomes 10 or 11.

In certain embodiments the sunflower plant, or progeny plant thereof, is further defined as an agronomically elite plant. Also provided in certain embodiments is a part of such a sunflower plant or progeny thereof, further defined as pollen, an ovule, a leaf, an embryo, a root, a root tip, an anther, a flower, a fruit, a stem, a shoot, a seed, a protoplast, a cell, and a callus. Another embodiment provides a seed that produced such a plant.

Certain embodiments provide a sunflower plant comprising at least a first introgressed sunflower chromosomal region conferring resistance to *Verticillium* wilt, wherein the region is selected from the group consisting of: a *Verticillium* wilt resistance contributing major QTL region found on chromosome 10, a *Verticillium* wilt resistance contributing minor QTL region found on chromosome 10, and a *Verticillium* wilt resistance contributing QTL region found on chromosome 11. In further embodiments, the invention provides a sunflower plant comprising at least two introgressed sunflower chromosomal regions selected from said group.

Also provided is a sunflower plant wherein the first introgressed sunflower chromosomal region conferring resistance to *Verticillium* wilt comprises an allele present in CN8861R.

DETAILED DESCRIPTION OF THE INVENTION

Figure 1:
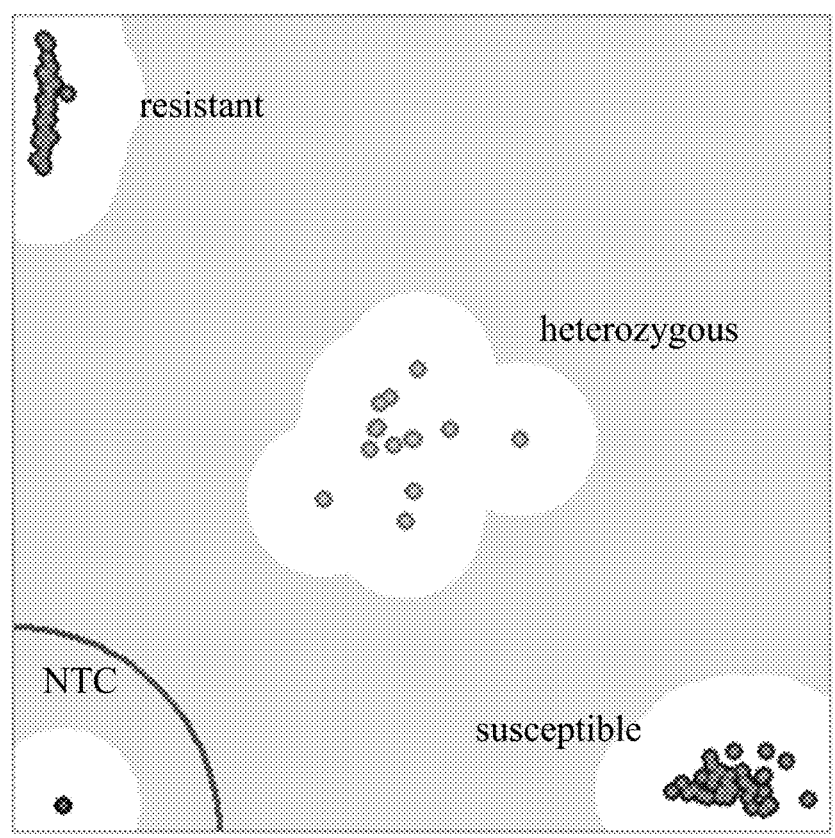
FIG. 1 depicts a distribution graph for a BC1F1 population based on Relative Fluorescence Units (RFU). Clusters for the resistant, heterozygous and susceptible genotypes are shown. NTC represents the no template controls.

The invention provides methods for identifying sunflower plants (*Helianthus annuus*) having resistance to *Verticillium* wilt caused by a *Verticillium* species, including *Verticillium dahliae*. Such sunflower lines can be referred to as *Verticillium* wilt resistant sunflower varieties. Methods of breeding *Verticillium* wilt resistant sunflower lines are further provided. Also disclosed herein are molecular markers that are linked to quantitative trait loci contributing to *Verticillium* wilt resistance. Through use of the markers, one of skill in the art may increase the degree of *Verticillium* wilt resistance in sunflower or select plants for an increased predisposition for *Verticillium* wilt resistance. In particular embodiments, the methods are performed on progeny sunflower plants of sunflower line CN8861R, such as members of the F2, F3, or F4 mapping populations disclosed herein, or progeny thereof.

The QTLs identified in this manner may be combined with one or more other QTLs that also contribute to *Verticillium* wilt resistance, as desired. In addition to the major QTL identified in FIG. 2 (localized to chromosome 10: 46.5-54.7 cM as identified in FIG. 2, two other minor QTLs were identified, one on chromosome 10 at 8.8 cM and another on chromosome 11 at 85.4 cM (see FIG. 2 and FIG. 3), also having significant effect on *Verticillium* wilt resistance in sunflower. Individually, each allele of these two QTLs is estimated to have the potential to significantly reduce a plant's *Verticillium* wilt disease rating in a *Verticillium* wilt pathology test as described herein when grown in multiple tested geographic locations.

As used herein, a "susceptible control sunflower plant" refers to a sunflower plant susceptible to *Verticillium* wilt (*Verticillium* wilt susceptible) including commercially available and wild relatives of modern sunflower plants. In one aspect, the control sunflower plant is the variety ONN120R. A "resistant control sunflower plant" may also be utilized when evaluating *Verticillium* wilt resistant sunflower varieties. In one embodiment, such a control is a sunflower plant that is not susceptible to *Verticillium* wilt, for example, variety CN8861R. As described herein, a control sunflower line is grown under similar environmental conditions as the comparative sunflower line, according to the present disclosure.

As used herein, a "hybrid sunflower plant" includes a plant resulting directly or indirectly from crosses between populations, breeds or cultivars within the species *Helianthus annuus*. "Hybrid sunflower plant" as used herein also refers to plants resulting directly or indirectly from crosses between different varieties or genotypes.

As used herein, "oil-type sunflowers" are sunflowers grown for crushing to make sunflower seed oil.

As used herein, "confection-type sunflowers" are sunflowers grown to produce seed, which is consumed whole, as a snack, bird food, or other kind of food, or is dehulled, and consumed as a seed, as a snack, or an ingredient in food.

As used herein, a "female parent" refers to a sunflower plant that is the recipient of pollen from a male donor line, which pollen successfully pollinates an egg. A female parent can be any sunflower plant that is the recipient of pollen. Such female parents can be male sterile, for example, because of genic male sterility, cytoplasmic male sterility, or because they have been subject to manual emasculation of the stamens.

As used herein, "cytoplasmic male sterility" refers to plants that are not usually capable of breeding from self-pollination, but are capable of breeding from cross-pollination.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with *Verticillium* wilt resistance. Stringent conditions for hybridization of a nucleic acid probe or primer to a marker sequence or a sequence flanking a marker sequence refers, for instance, to nucleic acid hybridization conditions of 5×SSC, 50% formamide, and 42° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, etc.

As used herein, a "desirable trait" or "desirable traits" that may be introduced into *Verticillium* wilt resistant sunflower plants by breeding may be directed to the sunflower fruit or the sunflower plant. Desirable traits to be introduced into sunflower plants and sunflower fruit may be independently selected. Desirable sunflower seed traits, e.g. as displayed by agronomically elite lines or cultivars, and that may be independently selected include, but are not limited to: seed size, shape, color, surface appearance; seed number, seed size, locule number; pericarp thickness and toughness; taste, bitterness, the presence of tubercles, and shelf life. Desirable sunflower plant traits, e.g. as displayed by agronomically elite lines or cultivars, and that may be independently selected include, but are not limited to: plant vigor, leaf shape, leaf length, leaf color, plant height, whether the plant is determinate or not, time to maturity, adaptation to field growth, adaptation to greenhouse growth, and resistance to one or more diseases or disease causing organisms such as Downey mildew, root knot nematodes, Tobacco Mosaic Virus, Sunflower scab, Anthracnose race 1, Powdery mildew (e.g. caused by *Erysiphe cichoracearum* or *Sphaerotheca fuliginea*), Target spot, Sunflower Mosaic Virus and *Fusarium* wilt. Any combination of desirable sunflower fruit traits, sunflower plant traits, or sunflower plant and fruit traits may be combined with a *Verticillium* wilt resistance trait. The resulting agronomically elite *Verticillium* wilt resistant sunflower plants of the present invention surprisingly display such agronomic traits in combination with *Verticillium* wilt resistance, while lacking deleterious traits.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

As used herein, "genotype" is the actual nucleic acid sequence at a locus in an individual plant. As used herein, "phenotype" means the detectable characteristics (e.g. level of *Verticillium* wilt resistance) of a cell or organism which can be influenced by genotype.

Positive additive effect generally means that a QTL is derived from the donor (in this case resistant) parent, and negative additive effect generally means that a QTL is derived from the elite (but susceptible) parent. In this case, however, the donor parent is an elite parent, and the susceptible parent is not. So, here, the negative additive effect of the minor QTL is due to the QTL originating from the susceptible parent.

*Verticillium* wilt resistance of a sunflower plant provided herein can potentially be defined as complete resistance or partial resistance. The *Verticillium* wilt resistance of a sunflower plant provided herein can be measured by any means available in the art.

In one aspect, *Verticillium* wilt resistance of a sunflower plant is determined by using a disease rating resistance or susceptibility. A disease rating resistant indicates a plant that demonstrates relative resistance when compared with a susceptible plant.

In another aspect, *Verticillium* wilt resistance is determined by obtaining disease ratings of symptom development after one or more rounds of inoculation or infection with *Verticillium* wilt on sunflower leaves and/or stems.

Resistance in a leaf test may be scored on an exemplary scale as follows:

TABLE 1

Index Value Symptoms

| Index Value | Symptoms |
|---|---|
| 1 | Absence of symptoms |
| 2 | Few small necrotic lesions without expansion |
| 3 | Few chlorotic and some necrotic lesions with limited expansion |
| 4 | Large expanding angular chlorosis with limited necrotic lesions |

Tests are evaluated once symptoms have developed on susceptible checks (e.g. cultivar ONN120R). CN8861R may be used as a "resistant" control. Observations are made of 12 plants in each plot. A row is classified as resistant, segregating, or susceptible based on the rate of resistant versus susceptible plants in each row. Each population was scored for the disease symptoms present on leaves and stems. Leaf symptoms were scored on a scale of 0-4 (0 being resistant and 4 highly susceptible, as set forth in Table 1) and were less informative due to similar symptoms for other sunflower diseases. Stem symptoms, which are more definitive for the disease, were scored during the later growth stage after the plants were completely matured and stalks were dried and brown. Individual plants in each row were scored either resistant or susceptible based on the observation of the disease symptoms after splitting open the stem vertically. Varieties are generally trialed several times before a final disease resistance level determination is made.

The *Verticillium* wilt resistant sunflower plants of the present invention may bear one or more alleles conferring *Verticillium* wilt resistance that have been introduced into the sunflowers from a line designated CN8861R comprising the *Verticillium* wilt resistance. The resulting *Verticillium* wilt resistant sunflower plants of the present invention surprisingly display elite agronomic traits in combination with *Verticillium* wilt resistance, while lacking deleterious traits.

In one aspect of the invention, a plant is assayed for *Verticillium* wilt resistance, partial resistance or susceptibility by image analysis of foliar tissue using about 3 leaves per plant captured in a digital image. The image analysis is conducted to determine the percentage of tissue damage and derive a disease rating. Image analysis software and methods used for quantifying visual differences in two or three dimensions are those set forth in Bright, 1987 (J. Microscopy 148:51-87) and Bickmore et al., 1999 (Geol. Mat. Res. 1(5):1-19). With respect to image analysis: "very resistant" exhibits between about 0% and 5% leaf area symptoms of chlorotic and/or necrotic lesions; "resistant" is between about 1% and 20% of the leaf area having symptoms of chlorotic and/or necrotic lesions; "substantially resistant" is between about 20% and 30% of the leaf area having symptoms of chlorotic and/or necrotic lesions; "mid-resistant" is between 40% and 50% of the leaf area having symptoms of chlorotic and/or necrotic lesions; "partially resistant" is less than or equal to about 50% of the leaf area having symptoms of chlorotic and/or necrotic lesions; "mid-susceptible" is between about 50% and 60% of the leaf area having symptoms of chlorotic and/or necrotic lesions; and "susceptible" is between about 60% and 100% of the leaf area having symptoms of chlorotic and/or necrotic lesions. A resistant plant can be characterized by other aspects as set forth herein, or by the use of other means, such as quantitative PCR to determine the level of infection.

Sunflower lines having *Verticillium* wilt resistance, or partial resistance, demonstrate a reduced level of symptoms relative to a non-resistant control sunflower line after inoculation or infection with *Verticillium* wilt. The level of symptoms can be used as an indicator of *Verticillium* wilt resistance. Disease symptoms measured can be any disease symptoms associated with *Verticillium* wilt infection. Symptoms can be selected from the group consisting of leaf blisters, necrosis, soft fruits, mosaic, chlorotic veins, chlorotic leaf spots, chlorotic and/or light green mosaic on leaves, fruit lesions, or combinations thereof. In one aspect, a *Verticillium* wilt resistant sunflower line demonstrates a reduction of foliar symptoms of chlorotic and/or necrotic lesions of at least, or greater than, 10%, 20%, 25%, 30%, 40%, 50%, 60%, 70%, 75%, 80%, 85%, 90%, 95%, or 98% relative to a non-resistant control sunflower line. In other aspects, the leaves of a *Verticillium* wilt resistant sunflower plant demonstrate less than 15%, or less than 10%, or less than 5%, or less than 2% symptomatic area when exposed to *Verticillium* wilt. In another aspect, the sunflower plant belongs to a sunflower variety or cultivar, and in another aspect, the sunflower plant is an inbred sunflower plant.

In another aspect, the sunflower plants and varieties provided herein demonstrate little or no symptoms of chlorotic and/or necrotic lesions after inoculation or infection with *Verticillium* wilt. In some aspects, a *Verticillium* wilt resistant sunflower plant demonstrates symptoms of chlorotic and/or necrotic lesions on less than 10%, 9%, 8%, 7%, 6%, 5%, 4%, 3% 2%, or 1% of the sunflower leaf surface.

*Verticillium* wilt resistant sunflower plants may exhibit a delay in the onset of symptoms of chlorotic and/or necrotic lesions relative to a non-resistant control sunflower plant. In some embodiments, the *Verticillium* wilt resistant sunflower plants exhibit a delay of 1, 2, 3, 4, 5, 6, 7, 8, 9, 10, 11, 12, 13, 14, or more days in the onset of symptoms of chlorotic and/or necrotic lesions relative to a control sunflower plant. In other embodiments, the *Verticillium* wilt resistant sunflower plants exhibit a delay of at least 7 or more days, 10 or more days, or 14 or more days in the onset of symptoms of chlorotic and/or necrotic lesions relative to a control sunflower plant.

In one aspect, the sunflower plant is a seedling at the time of inoculation or infection. In some aspects, the sunflower plant is a seedling at the 4, 5, 6, 7, or 8 leaf stage of development when inoculated. In one aspect, disease symptoms can be measured at any time after pathogenic challenge of a sunflower plant. In other aspects, symptoms can be measured 2, 3, 4, 5, 6, 7, 8, 9, 10, 11, 12, 13, 14, 15, 16, 17, 18, 19, 20, 21, or more days after inoculation. In another aspect, the sunflower plant is any age of plant at the time of inoculation or infection.

In another aspect, disease symptoms can be observed after *Verticillium* wilt challenge of an entire plant or a part thereof, for example, a plant cutting.

*Verticillium* wilt resistant sunflower plants of the present invention may exhibit an increase in fruit yield after inoculation or infection with *Verticillium* wilt relative to a control sunflower plant inoculated with *Verticillium* wilt. In one aspect, the resistant sunflower plants exhibit a 2%, 5%, 10%, 15%, 20% or more increase in fruit yield, based upon the total mass, number, or total volume of fruit, relative to a control sunflower plant after one or more rounds of inoculation or infection with *Verticillium* wilt.

The present invention provides for and includes sunflower plants that exhibit resistance to one or more races of *Verticillium* wilt. In some embodiments, the sunflower plants of the present invention exhibit resistance to 1, 2, 3, 4, 5, 6, 7, 8, 9, 10, or more races of *Verticillium* wilt.

The present invention provides for a seed of a sunflower plant capable of producing a plant having *Verticillium* wilt resistance. In one aspect, the sunflower plant can be an open-pollinated variety, a hybrid parent inbred line, or a male sterile line. In another aspect, the invention provides seed of a sunflower plant capable of producing a hybrid sunflower plant having *Verticillium* wilt resistance.

The sunflower plants of the present invention can be sunflower lines adapted for greenhouse sunflower production or for field sunflower production. In one aspect, the sunflower plants of the present invention are adapted for greenhouse sunflower production.

The present invention also provides a hybrid sunflower having *Verticillium* wilt resistance. In another aspect, the present invention provides a hybrid sunflower exhibiting *Verticillium* wilt resistance after inoculation or infection with *Verticillium* wilt.

Commercially valuable sunflower plants represent one aspect of the present invention. In one aspect, certain sunflower traits, including, for example, fruit size, shape, color, weight, taste and fruit yield may be important to the commercial value of the crop. Seed size, and shape, may be of particular interest if the sunflowers are grown for oil or for confection. The present invention provides for a sunflower plant that produces a sunflower seed having a length of about, or greater than about, 5, 6, 7, 8, 9, 10, 11, 12, 13, 14, or 15 mm in oil-type sunflowers, and greater than about, 5, 6, 7, 8, 9, 10, 11, 12, 13, 14, 15, 16, 17, 18, 19, 20, 21, 22, 23, 24, 25, 26, 27, 28, 29 or 30 mm in confection-type sunflowers.

In some aspects, a sunflower plant of the present invention may produce a sunflower seeds having a total weight (per 1000 seeds) at harvest of about or greater than about 40, 45, 50, 55, 60, 65, 70, 75, 80 or 85 grams for oil-type sunflowers and 40, 45, 50, 55, 60, 65, 70, 75, 80, 85, 90, 95, 100, 105, 110, 115, 120, 125, 130, 135, 140, 145, 150, 155, 160, 165, or 190 grams for confection-type sunflower. In other aspects, a sunflower plant of the present invention produces sunflower seeds having a total weight at harvest between about 80 and about 125 grams, about 90 and about 115 grams, about 100 and about 120 grams, about 90 and about 125 grams, about 95 and about 125 grams, about 100 and about 125 grams, or between about 115 and about 125 grams. Seed weight is measured by weighing the seeds from individual sunflower heads on a scale.

A sunflower head attribute such as shape, weight, size, or seed count can be measured or evaluated at a variety of times. In one aspect, an attribute is measured following growth in a growth chamber. In another aspect, an attribute is measured at the time of harvest.

In one embodiment, a sunflower head from a sunflower plant having *Verticillium* wilt resistance has an overall head or seed quality rating of 1, 3, 5, 7, or 9, where fruit quality is measured by visual inspection, with a scale ranging from 1=excellent through 9=poor: Rating 1=Excellent; 3=Above average; 5=Average; 7=Below average; 9=Poor; compared to the standard commercial hybrids grown in the area. Seed or quality relates to seed color, seed shape, seed length, diameter and oil content. Head quality relates to head shape, head length, head weight, and seed count.

In yet another aspect, tissue culture of the sunflower plants described herein relates to the culture of protoplasts, calli, or plant cells, that are isolated from, or present in, intact parts of the *Verticillium* wilt resistant plants described herein.

Once *Verticillium* wilt resistant plants are produced, the plants themselves can be cultivated in accordance with conventional procedures. *Verticillium* wilt resistant progeny may be obtained through sexual reproduction. The seeds resulting from sexual reproduction can be recovered from the fruit of *Verticillium* wilt resistant plants and planted or otherwise grown as a means of propagation. *Verticillium* wilt resistant progeny may also be obtained from *Verticillium* wilt resistant plants through asexual reproduction. Protoplast or propagules (e.g., cuttings, scions or rootstocks) can be recovered from *Verticillium* wilt resistant plants or parts thereof and may be employed to propagate *Verticillium* wilt resistant plants.

The present invention also provides for and includes a container of sunflower seeds in which sunflower plants grown from greater than 50% of the seeds have resistance or partial resistance to *Verticillium* wilt. In another aspect, sunflower plants grown from greater than 55%, 65%, 75%, 85%, 90%, 95%, 98%, or 99% of the sunflower seeds in the container have *Verticillium* wilt resistance. Another aspect of the invention relates to seeds from a sunflower plant selected from the group consisting of: CN8861R and progeny of CN8861R. *Verticillium* wilt resistant progeny thereof, wherein sunflower plants grown from about 50%, or greater than 50%, of the seeds have resistance or partial resistance to *Verticillium* wilt.

The container of sunflower seeds can contain any number, weight or volume of seeds. For example, a container can contain about, or greater than about, 10, 25, 50, 200, 400, 700, 1000, 2000, 3000, or more seeds. In another aspect, a container can contain about, or greater than about, 1 gram, 5, 10, 15, 25, 100, 250, 500, or 1,000 grams of seeds. Alternatively, the container can contain about or at least, or greater than, about 1 ounce, 2, 4, 8, 10 ounces, 1 pound, 2, 4, 8, 12 pounds or more of seeds. Containers of sunflower seeds can be any container available in the art. For example, a container can be a box, a bag, a packet, a pouch, a tape roll, a foil, a pail, or a tube.

One aspect of the invention relates to dried, or otherwise processed, sunflower seeds, produced by a sunflower plant having a genome that comprises at least one genetic locus giving rise to *Verticillium* wilt resistance when expressed in a sunflower plant. Processed sunflower seed or head includes, but is not limited to dried or processed sunflower seeds.

The present invention provides for an inbred sunflower plant having resistance to *Verticillium* wilt, wherein the resistance is exhibited when the plant is in contact with *Verticillium* wilt. In one aspect, the inbred sunflower plant is derived from accession CN8861R.

The present invention includes and provides for *H. annuus* plants having at least one allele for a *Verticillium* wilt resistance trait. The *Verticillium* wilt resistant sunflower plants can be either heterozygous or homozygous for the *Verticillium* wilt resistance trait. In one embodiment, the *Verticillium* wilt resistant trait can be linked to variations in a single gene (e.g., linked to one or more alleles of a single gene). In another embodiment, the *Verticillium* wilt resistance trait can be linked to variations at one or one or more quantitative trait loci (QTL). In a yet another embodiment, the *Verticillium* wilt resistant sunflower plants are homozygous for the *Verticillium* wilt resistance trait.

The present invention provides progeny of sunflower plants having resistance to *Verticillium* wilt. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a *Verticillium* wilt resistant sunflower plant and expresses the genetic material that provides *Verticillium* wilt resistance. Representative populations of sunflower plants comprising progeny having resistance to *Verticillium* wilt include progeny of the cross of susceptible parent (ONN120R)×the resistant parent (CN8861R).

One embodiment of the present invention provides for a *Verticillium* wilt resistant sunflower plant that contains a genetic marker linked to one or more *Verticillium* wilt resistance locus. By "*Verticillium* wilt resistance locus" is meant a locus that contributes to *Verticillium* wilt resistance either alone or in combination with one more other *Verticillium* wilt resistance locus. By "contributes to *Verticillium* wilt resistance" it is meant that the degree of *Verticillium* wilt resistance is increased in the corresponding plant, either when the locus is alone or in combination with one or more other locus.

In one embodiment of the invention, a marker linked to one or more *Verticillium* wilt resistance loci includes one or more of the following: CN8861R and CN8862R. In another embodiment of the invention, the assayed markers linked to one or more *Verticillium* wilt resistance loci include each of the following: CN8861R and CN8862R. In yet another embodiment, the marker(s) linked to one or more *Verticillium* wilt resistance loci includes one or more SNP marker(s) selected from the group consisting of: comprising a single nucleotide polymorphism of one of SEQ ID NOs:1-7.

As used herein, linkage of two nucleic acid sequences, including a nucleic acid marker sequence and a nucleic acid sequence of a genetic locus imparting a desired trait such as *Verticillium* wilt resistance, may be genetic or physical or both. In one aspect of the invention, the nucleic acid marker and genetic locus conferring *Verticillium* wilt resistance are genetically linked, and exhibit a LOD score of greater than 2.0, as judged by interval mapping for the *Verticillium* wilt resistance trait based on maximum likelihood methods described by Lander and Botstein, 1989 (Genetics, 121:185-199), and implemented in the software package MAPMAKER (e.g. Lander et al., Genomics 1:174-181, (1987); default parameters). Alternatively, other software such as QTL Cartographer vl 0.17 (Basten et al., Zmap—a QTL cartographer. In: Proceedings of the 5th World Congress on Genetics Applied to Livestock Production: Computing Strategies and Software, edited by C. Smith, J. S. Gavora, B. Benkel, J. Chesnais, W. Fairfull, J. P. Gibson, B. W. Kennedy and E. B. Burnside. Volume 22, pages 65-66. Organizing Committee, 5th World Congress on Genetics Applied to Livestock Production, Guelph, Ontario, Canada, 1994; and Basten et al., QTL Cartographer, Version 1.17. Department of Statistics, North Carolina State University, Raleigh, N.C., 2004) may be used. Mapping of QTLs is well-described (e.g. WO 90/04651; U.S. Pat. Nos. 5,492,547, 5,981,832, 6,455,758; reviewed in Flint-Garcia et al. 2003 (Ann. Rev. Plant Biol. 54:357-374, the disclosures of which are hereby incorporated by reference).

In other embodiments, the marker and region conferring *Verticillium* wilt resistance are genetically linked and exhibit a LOD score of greater than 3.0, or a LOD score of greater than 6.0, 9.0, 12.0, 15.0, or 18.0. In one embodiment, the marker and region contributing to *Verticillium* wilt resistance are genetically linked and exhibit a LOD score of between about 14 and about 20. When assigning the presence of a QTL, the LOD threshold score associated with a QTL analysis as described herein may be determined to be significant at the 95% confidence level, or higher, such as at the 98% or 99% confidence level.

In another aspect, the nucleic acid marker is genetically linked at a distance of between about 0 and about 50 centimorgans (cM) to the *Verticillium* wilt resistance locus. In other embodiments, the distance between the nucleic acid marker and the *Verticillium* wilt resistance locus is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

In yet another aspect, the invention provides a sunflower plant comprising an introgressed chromosomal region from chromosome 10 of CN8861R or a progeny plant thereof, of 20 cM, 10 cM, 5 cM, or 1 cM within the region defined as spanning the positions of SNP marker DHAG001106 and SNP marker DHAI006271.

In still yet another aspect, the invention provided a sunflower plant comprising an introgressed chromosomal region from chromosome 10 of CN8861R or a progeny plant thereof, of 20 cM, 10 cM, 5 cM, or 1 cM within the region defined as spanning the positions of SNP marker DHAI005760 and SNP marker DHAI006271 or SNP marker DHAI000041 and SNP marker DHAI006271.

In yet another aspect, the invention provides a sunflower plant comprising an introgressed chromosomal region from chromosome 10 of CN8861R or a progeny plant thereof, of 20 cM, 10 cM, 5 cM, or 1 cM within the region tightly linked to the positions of SNP marker DHAG000460. In still other embodiments, the sunflower plant may comprise an introgressed chromosomal region of chromosome 11 from CN8861R or a progeny plant thereof, of 20 cM, 10 cM, 5 cM, or 1 cM within the region tightly linked to the positions of SNP marker DHAI007648.

In still other embodiments, the sunflower plant may comprise an introgressed chromosomal region of chromosome 10 and a second introgressed chromosomal region of chromosome 10 of CN8861R wherein the introgressed chromosomal regions allow for enhanced resistance to *Verticillium* wilt, relative to an otherwise isogenic sunflower line not comprising one or more of the introgressed region(s).

In still other embodiments, the sunflower plant may comprise an introgressed chromosomal region of chromosome 10 and a second introgressed chromosomal region of chromosome 11 of CN8861R, wherein the introgressed chromosomal regions allow for enhanced resistance to *Verticillium* wilt, relative to an otherwise isogenic sunflower line not comprising one or more of the introgressed region(s).

In still other embodiments, the sunflower plant may comprise an introgressed chromosomal region of chromosome 10 and a second introgressed chromosomal region of chromosome 10, and a third introgressed chromosomal region of chromosome 11 of CN8861R wherein the introgressed chromosomal regions allow for enhanced resistance to *Verticillium* wilt, relative to an otherwise isogenic sunflower line not comprising one or more of the introgressed region(s).

In another aspect, the nucleic acid marker sequence may be physically linked to a *Verticillium* wilt resistance locus. In some aspects, the nucleic acid sequence of the genetic marker specifically hybridizes to a nucleic acid molecule having a sequence that is within about 30 Mbp, or about 20 Mbp, or about 15 Mbp, or about 10 Mbp, or about 5 Mbp of a *Verticillium* wilt resistance locus. In another aspect, the nucleic acid sequence of the genetic marker specifically hybridizes to a nucleic acid molecule having a sequence of any of SEQ ID NOs:1-7, or a complement thereof.

As used herein, two nucleic acid molecules are said to be capable of hybridizing to one another if the two molecules are capable of forming an anti-parallel, double-stranded nucleic acid structure. Conventional stringency conditions are described by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×. sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. In some embodiments, hybridization conditions can be high, moderate or low stringency conditions. Preferred conditions include those using 50% formamide, 5.0×. SSC, 1% SDS and incubation at 42° C. for 14 hours, followed by a wash using 0.2×SSC, 1% SDS and incubation at 65° C.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

In particular embodiments, these markers may be genetically linked to the described QTLs for *Verticillium* wilt resistance which are located on sunflower chromosomes 10 and 11. In certain embodiments, the markers are within 50 cM, 45 cM, 40 cM, 30 cM, 20 cM, 10 cM, 9 cM, 8 cM, 7 cM, 6 cM, 5 cM, 4 cM, 3 cM, 2 cM, 1 cM, or less, of the major QTL defined on chromosome 10; or the minor QTL defined on chromosome 10; or the minor QTL defined on chromosome 11, based on analysis of the F4 mapping populations as described herein. In particular embodiments, the markers used to follow the presence of any of these QTLs for *Verticillium* wilt resistance which are located on sunflower chromosomes 10 or 11, are selected from the group consisting of: comprising a single nucleotide polymorphism of one of SEQ ID NOs:1-7 as shown in Table 2 or other genetic markers linked to any of these QTLs. The presence of alleles conferring resistance to *Verticillium* wilt may be identified by use of well-known techniques, such as by nucleic acid detection methods utilizing probes or primers comprising a sequence selected from the group consisting of SEQ ID NO:1-7. In certain embodiments, the method comprises detecting the presence of one or more single nucleotide polymorphisms (SNP's) given in one or more of SEQ ID NOs:1-7.

In certain embodiments, the *Verticillium* wilt resistance QTLs of chromosome 10 are defined as spanning the region defined by SNP marker DHAG001106 to SNP marker DHAG006271. In other embodiments, the *Verticillium* wilt resistance major QTL of chromosome 10 is defined as spanning the region defined by SNP marker DHAI005760 to SNP marker DHAG006271. In another embodiment, the *Verticillium* wilt resistance major QTL of chromosome 10 is defined as spanning the region defined by SNP marker DHA0000041 and DHAG006271

In certain embodiments, the *Verticillium* wilt resistance QTL of chromosome 11 is defined as tightly linked to SNP marker DHAI007648. Tightly linked, as used herein, means within 8, 7, 6, or 5cM from the marker.

In other embodiments, the *Verticillium* wilt resistance minor QTL of chromosome 10 is defined as tightly linked to SNP marker DHAG000460.

The major QTL has also been defined in a mapping population based on a cross of sunflower lines ONN120R and CN8861R, as being located between genetic markers DHAI005760 and DHAI006271, at about 46.5cM-54.7 cM in the linkage group, and as defined by analysis of that mapping population. Further, one of skill in the art would understand that assignment of such genetic map positions may be affected by the mapping population being analyzed, including for instance the parent lines used, the marker density, and the size of the population, each of which may affect the level of recombination which is seen, and thus the assigned genetic map position, An integrated genetic and physical map may be utilized to define the position of a sunflower QTL for instance relative to markers with known genetic and/or physical map positions.

The minor QTL have also been defined in a mapping population based on a cross of sunflower lines ONN120R and CN8861R, as being located at genetic marker DHAI007648, at about 85.4 cM in the linkage group on chromosome 11, and being located at genetic marker DHAG000460, at about 8.8cM in the linkage group on chromosome 10, and as defined by analysis of that mapping population. Further, one of skill in the art would understand that assignment of such genetic map positions may be affected by the mapping population being analyzed, including for instance the parent lines used, the marker density, and the size of the population, each of which may affect the level of recombination which is seen, and thus the assigned genetic map position. An integrated genetic and physical map may be utilized to define the position of a sunflower QTL for instance relative to markers with known genetic and/or physical map.

The definition of these QTLs allows the use of specific molecular markers, such as those disclosed herein, in a plant breeding program to introgress a Verticillium wilt resistance trait or traits into agronomically acceptable sunflower lines. Marker-assisted introgression involves the transfer of a chromosomal region, defined by one or more markers, from one germplasm to a second germplasm. An initial step in that process is the localization of the trait by gene mapping which is the process of determining the position of a gene relative to other genes and genetic markers through linkage analysis. The basic principle for linkage mapping is that the closer together two genes are on the chromosome, the more likely they are to be inherited together. Briefly, a cross is made between two genetically compatible but divergent parents relative to a trait under study (e.g. Verticillium wilt resistance). Genetic markers are then used to follow the segregation of traits under study in the progeny from the cross, often termed a "mapping population." The current invention relates to the introgression in sunflower of genetic material, e.g., mapping to one or more QTLs, which is capable of causing a plant to be more resistant to the pathogen which causes sunflower Verticillium wilt. The present inventors have identified chromosomal regions responsible for enhanced Verticillium wilt resistance and used marker assisted breeding to introgress these specific linkage blocks into other sunflower germplasm which lacked such resistance to Verticillium wilt. In certain embodiments of the invention, the process for producing Verticillium wilt resistant sunflower plant or line comprises introgressing at least one chromosomal locus mapping to a QTL on chromosome 10 or chromosome 11 from a more Verticillium wilt resistant sunflower plant, line, or variety into a less Verticillium wilt resistant sunflower plant, line, or variety. In specific embodiments, the more Verticillium wilt resistant sunflower plant, line, or variety is CN8861R, or a progeny plant thereof.

Introgression of a particular DNA element or set of elements into a plant genotype is defined as the result of the process of backcross conversion. A plant genotype into which a DNA sequence has been introgressed may be referred to as a backcross converted genotype, line, or variety. Such genotype, line, or variety may be an inbred or a hybrid genotype, line, or variety. Similarly a plant genotype lacking said desired DNA sequence may be referred to as an unconverted genotype, line, or variety. During breeding, the genetic markers linked to enhanced Verticillium wilt resistance may be used to assist in breeding for the purpose of producing sunflower plants with increased resistance to Verticillium wilt. A skilled worker would understand that the introgression of a Verticillium wilt resistance trait into a sunflower plant may be monitored by visual clues such as by use of a disease resistance test with a disease rating scale as described herein, and/or by monitoring and breeding for the presence of molecular markers as described herein (i.e. marker assisted selection).

Localization of such markers to specific genomic regions or contigs further allows for use of associated sequences in breeding, to develop additional linked genetic markers, as well as to identify the mechanism for resistance at more precise genetic and biochemical levels. It will be understood to those of skill in the art that other markers or probes which more closely map the chromosomal regions as identified herein could be employed to identify plants comprising a desired QTL for Verticillium wilt resistance. The chromosomal regions of the present invention facilitate introgression of increased Verticillium wilt resistance from Verticillium wilt resistant germplasm, such as CN8861R or progeny thereof, into other germplasm, preferably agronomically useful sunflower germplasm. Linkage blocks of various sizes could be transferred within the scope of this invention as long as the chromosomal region enhances the Verticillium wilt resistance of a desirable sunflower plant, line, or variety. Accordingly, it is emphasized that the present invention may be practiced using any molecular markers which genetically map in similar regions, provided that the markers are polymorphic between the parents.

In one aspect, the invention provides a method of obtaining sunflower germplasm comprising the steps of: a) assaying sunflower plants for the presence of at least a first genetic marker genetically linked to a QTL that confers resistance to Verticillium wilt; and b) selecting at least a first sunflower plant comprising the genetic marker and the QTL that confers resistance to Verticillium wilt; wherein the QTL maps to a position between the sequence represented by SNP markers DHAG001 106 and DHAG006271 which map to approximately 0 cM and 54.7 cM on the genetic map of the sunflower chromosome 10.

In another aspect, the invention provides a method of obtaining sunflower germplasm comprising the steps of: a) assaying sunflower plants for the presence of at least a first genetic marker genetically linked to a QTL that confers resistance to Verticillium wilt; and b) selecting at least a first sunflower plant comprising the genetic marker and the QTL that confers resistance to Verticillium wilt; wherein the major QTL maps to a position between the sequence represented by SNP markers DHAI005760 and DHAI006271 which map to approximately 46.5cM and 54.7cM (approximately 8.2 cM apart) on the genetic map of sunflower chromosome 10.

In another aspect, the invention provides a method of obtaining sunflower germplasm comprising the steps of: a) assaying sunflower plants for the presence of at least a first genetic marker genetically linked to a QTL that confers resistance to Verticillium wilt; and b) selecting at least a first sunflower plant comprising the genetic marker and the QTL that confers resistance to Verticillium wilt; wherein the major QTL maps to a position between the sequence represented by SNP markers DHAI000041 and DHAI006271 which map to approximately 47.2 cM and 54.7 cM (approximately 7.5 cM apart) on the genetic map of sunflower chromosome 10.

In another aspect, the invention provides a method of obtaining sunflower germplasm comprising the steps of: a) assaying sunflower plants for the presence of at least a first genetic marker genetically linked to a QTL that confers resistance to *Verticillium* wilt; and b) selecting at least a first sunflower plant comprising the genetic marker that confers resistance to *Verticillium* wilt; wherein the minor QTL maps to a position near the sequence represented by SNP marker DHAG000460 on the genetic map of sunflower chromosome 10.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the F1 hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with *Verticillium* wilt resistance can be utilized (Walton, Seed World 22-29 (July, 1993); Burow and Blake, Molecular Dissection of Complex Traits, 13-29, Eds. Paterson, CRC Press, New York (1988)). Methods to isolate such markers and to design probes or primers useful in following the presence of such markers are known in the art. For example, locus-specific SSRs can be obtained by screening a sunflower genomic library for SSRs, sequencing of "positive" clones, designing primers which flank the repeats, and amplifying genomic DNA with these primers. Likewise, SNP markers may be identified as well.

The genetic linkage of marker molecules to *Verticillium* wilt resistance can be established by a gene mapping model such as, without limitation, the flanking marker model, and the interval mapping, based on maximum likelihood methods described by Lander and Botstein, 1989 (Genetics, 121:185-199), and implemented in the software packages MAPMAKER (Whitehead Institute for Biomedical Research, Cambridge Mass., USA) or QTL Cartographer (North Carolina State University, Bioinformatics Research Center) or the like.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, Plant Breeding, Hayward, Bosemark, Romagosa (eds.) Chapman & Hall, London, pp. 314-331 (1993), and van Ooijen (Heredity 83:613-624, 1999).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

Advanced breeding lines are collected from breeding programs. These are tested for their phenotype (e.g. their disease score reactions to *Verticillium* wilt), and genotyped for markers in the *Verticillium* wilt QTL intervals. From these data, the smallest genetic interval is identified within each QTL containing the donor parent (DP) favorable allele among the *Verticillium* wilt resistant lines. This interval is inferred to be critical for conferring resistance to *Verticillium* wilt. Candidate genetic intervals associated with *Verticillium* wilt resistance were detected as regions showing enhanced frequency of the favorable allele from the *Verticillium* wilt resistance donor CN8861R relative to a baseline set of *Verticillium* wilt susceptible samples from the same germplasm classification type (GCT). For example, comparisons may be made among *Verticillium* wilt resistant and susceptible inbreds within a single GCT and a single breeding program. Allele frequency shifts between phenotypic classes may be detected by calculating a linkage assessment score (LAS) as: LAS=(Frequency of favorable allele in samples with favorable phenotype)×(Frequency of unfavorable allele in samples with unfavorable phenotype).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants. As used herein, a second plant is derived from a first plant if the second plant's pedigree includes the first plant.

The present invention provides a genetic complement of the sunflower lines described herein. Further provided is a hybrid genetic complement, wherein the complement is formed by the combination of a haploid genetic complement from elite inbred sunflower lines described herein and another haploid genetic complement. Means for determining such a genetic complement are well-known in the art.

As used herein, the phrase "genetic complement" means an aggregate of nucleotide sequences, the expression of which defines the phenotype of a plant, such as a sunflower plant or a cell or tissue of that plant. By way of example, a sunflower plant is genotyped to determine a representative sample of the inherited markers it possesses. Markers are preferably inherited in codominant fashion so that the presence of both alleles at a diploid locus is readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified F2 population using a codominant marker system (Mather, Measurement of Linkage in Heredity: Methuen and Co., (1938)). An F2 population is the first generation of self or sib pollination after the hybrid seed is produced. Usually a single F1 plant is self or sib pollinated to generate a population segregating for the nuclear-encoded genes in a Mendelian (1:2:1) fashion.

In contrast to the use of codominant markers, using dominant markers often requires progeny tests (e.g., F3 or back cross self families) to identify heterozygous individuals. The information gathered can be equivalent to that obtained in a completely classified F2 population. This procedure is, however, often prohibitive because of the cost and time involved in progeny testing. Progeny testing of F2 individuals is often used in map construction where error is associated with single plant phenotyping, or when sampling the plants for genotyping affects the ability to perform accurate phenotyping, or where trait expression is controlled by a QTL. Segregation data from progeny test populations (e.g., F3 or backcrossed or selfed families) can be used in trait mapping. Marker-assisted selection can then be applied to subsequent progeny based on marker-trait map associations (F2, F3), where linkage has not been completely disassociated by recombination events (i.e., maximum disequilibrium).

Recombinant inbred lines (RILs) (genetically related lines; usually >F 5) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g. Reiter et al., 1992; Proc. Natl. Acad. Sci. (U.S.A.) 89:1477-1481). However, as the distance between markers becomes larger (i.e., loci become more independent), the information in RIL populations decreases dramatically when compared to codominant markers.

Backcross populations can be utilized as mapping populations. A backcross population (BC) can be created by crossing an F1 to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992; Proc. Natl. Acad. Sci. (U.S.A.) 89:1477-1481).

Information obtained from backcross populations using either codominant or dominant markers is less than that obtained from completely classified F2 populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., 1991; Proc. Natl. Acad. Sci. (U.S.A.) 88:9828-9832). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a *Verticillium* wilt resistant sunflower plant comprising: (a) crossing a sunflower line having *Verticillium* wilt resistance with a second sunflower line lacking *Verticillium* wilt resistance to form a segregating population; (b) screening the population for resistance to *Verticillium* wilt; and (c) selecting one or more members of the population having said *Verticillium* wilt resistance. In one aspect, the sunflower line having *Verticillium* wilt resistance is crossed with the second sunflower line for at least two generations (e.g., creating either an F2 or BC1S1 population). In a particular embodiment, the sunflower line having *Verticillium* wilt resistance is CN8861R, or a progeny thereof. In another aspect, plants are identified as *Verticillium* wilt resistant prior to crossing. In one aspect, plants can be selected on the basis of partial or complete resistance to *Verticillium* wilt. In one aspect, the segregating population is self-crossed and the subsequent population is screened for resistance.

In another aspect, the present invention provides a method of introgressing *Verticillium* wilt resistance into a sunflower plant comprising: (a) crossing at least a first sunflower line having *Verticillium* wilt resistance with a second sunflower line to form a segregating population; (b) screening said population for resistance to *Verticillium* wilt; and (c) selecting at least one member of said population exhibiting *Verticillium* wilt resistance. In one aspect, the sunflower line having *Verticillium* wilt resistance is crossed with the second sunflower line for at least two generations (e.g., creating either on F2 or BC1S1 population), or up to 2-10 generations. In another aspect, plants are identified as *Verticillium* wilt resistant prior to crossing. In one aspect, the segregating population is self-crossed and the subsequent population is screened for resistance.

Sunflower plants (and parts thereof, including seed, pollen, and ovules) generated using a method of the present invention are also provided, and can be part of or generated from a breeding program. The choice of breeding method depends on the mode of plant reproduction, the heritability of the trait(s) being improved, and the type of cultivar used commercially (e.g., F1 hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, fruit size, fruit quality, and/or fruit yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new sunflower lines requires the development and selection of sunflower varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an F1. An F2 population is produced by selfing one or several F1's. Selection of the best individuals in the best families is performed. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent. Cross breeding or backcross breeding of a *Verticillium* wilt resistant sunflower plant may be conducted where the other parent (second sunflower plant) is *Verticillium* wilt resistant or the other parent is not *Verticillium* wilt resistant.

Sunflower plants generated of the invention may be generated using a single-seed descent procedure. The single-seed descent procedure, in the strict sense, refers to planting a segregating population, then selecting one plant in this and each subsequent generation to self and create the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Descriptions of other breeding methods that are commonly used for different traits and crops can be found in one of several available reference books (e.g., Fehr, Principles of Cultivar Development Vol. 1, pp. 2-3 (1987)).

Another aspect of the invention is directed to an inbred sunflower plant having resistance to *Verticillium* wilt, wherein said resistance is exhibited when said plant is in contact with said *Verticillium* wilt, and wherein said sunflower plant is not derived from a plant selected from the group consisting of—CN8861R and progeny of CN8861R. Also included in the invention is a sunflower plant having a genome, wherein said genome comprises a genetic locus conferring resistance to *Verticillium* wilt, wherein said genetic locus contains one or more genetic markers linked to said genetic locus conferring resistance to *Verticillium* wilt, and wherein said sunflower plant is not accession CN8861R.

In another aspect, additional sources of *Verticillium* wilt resistance for use in a breeding program can be identified by screening sunflower germplasm for resistance to *Verticillium* wilt. In yet another aspect, sunflower plants can be screened for *Verticillium* wilt resistance by identifying germplasm exhibiting reduced disease symptoms relative to a control sunflower plant after inoculation or infection. In one aspect, sunflower plants can be screened for resistance to *Verticillium* wilt using a test such as a field or greenhouse screen and disease rating schemes as described herein.

In another aspect, additional sources of *Verticillium* wilt resistance for use in a breeding program can be identified by screening with one or more molecular markers linked to a genetic locus conferring resistance to *Verticillium* wilt, such as those identified herein.

In another aspect, additional sources of *Verticillium* wilt resistance for use in a breeding program can be identified by a combination of screening sunflower plants for reduced disease symptoms then screening with one or more molecular markers linked to a genetic locus contributing to resistance to *Verticillium* wilt.

In another aspect, sunflower lines having *Verticillium* wilt resistance can be used in breeding programs to combine *Verticillium* wilt resistance with additional traits of interest. In one aspect, *Verticillium* wilt resistance can be combined with any additional trait, including disease resistant traits, yield traits, and fruit quality traits. For example, breeding programs can be used to combine the *Verticillium* wilt resistance trait with alleles that contribute to size and shape in sunflower fruit. Breeding programs can also be used to combine *Verticillium* wilt resistance with one or more disease resistant traits. Such disease resistant traits include, without limitation, resistance to: *Verticillium* wilt, root knot nematodes, Tobacco Mosaic Virus, Sunflower scab, Powdery mildew, Target spot, Sunflower Mosaic Virus, and *Fusarium* wilt. In another aspect, the traits that are combined can be co-inherited in subsequent crosses.

The present invention also provides for parts of the *Verticillium* wilt resistant sunflower plants produced by a method of the present invention. Parts of sunflower plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a sunflower fruit, which include the placenta, columella and pericarp. In one embodiment of the present invention, the plant part is a seed.

The invention further provides for parts of a sunflower plant having a genome, that comprises at least one genetic locus giving rise to *Verticillium* wilt resistance in the sunflower plant. In another embodiment, parts of sunflower plants are derived from a sunflower plant selected from the group consisting of CN8861R and progeny of CN8861R.

In one embodiment, the invention provides a *Verticillium* wilt resistant sunflower plant, or the fruit or seeds thereof, wherein the sunflower plant demonstrates a reduction in foliar symptoms of chlorotic and/or necrotic lesions relative to a non-resistant control plant upon inoculation or infection with *Verticillium* wilt, and wherein said plant demonstrates resistance to one or more of *Verticillium* wilt, root knot nematodes, tobacco mosaic virus, sunflower scab, powdery mildew, target spot, sunflower mosaic virus, *papaya* ringspot virus, zucchini yellow mosaic virus, and *Fusarium* wilt. In other embodiments, a *Verticillium* wilt resistant sunflower plant that also demonstrates resistance to one or more of: *Verticillium* wilt, sunflower scab, powdery mildew, target spot, sunflower mosaic virus, nematodes, tobacco mosaic virus *papaya* ringspot virus, zucchini yellow mosaic virus, and *Fusarium* wilt displays a greater than 10% reduction, or a greater than 30% reduction, or a greater than 60% reduction in foliar symptoms of chlorotic and/or necrotic lesions upon inoculation or infection with *Verticillium* wilt. In some aspects, the sunflower plants are adapted either for greenhouse growth or for field growth.

One aspect of the invention provides a *Verticillium* wilt sunflower plant, or the fruit or seeds thereof, wherein the sunflower plant, or the fruit thereof, expresses one, or two, or three, or more independently selected desirable traits in addition to *Verticillium* wilt resistance. In one embodiment, the "desirable trait" or "desirable traits" are selected from the group consisting of: fruit size, shape, color, surface appearance; seed number, seed size, locule number; pericarp thickness and toughness; taste, bitterness, the presence of tubercles, and shelf life, plant vigor, leaf shape, leaf length, leaf color, plant height, whether the plant is determinate or not, time to maturity, adaptation to field growth, adaptation to greenhouse growth, and resistance to one or more diseases or disease causing organisms such as *Verticillium* Wilt, root knot nematodes, Tobacco Mosaic Virus, Sunflower Scab, Powdery Mildew, *Verticillium* wilt, Target Spot, Sunflower Mosaic Virus, and *Fusarium* Wilt. In another embodiment the "desirable trait" or "desirable traits" are selected from the group consisting of: fruit size, fruit shape, fruit color, fruit taste, the number of seeds per fruit, the size of seeds, the thickness of fruit pericarp tissue, the shelf life of fruit, resistance to *Verticillium* Wilt, resistance to Sunflower Scab, resistance to Powdery Mildew, resistance to Target Spot, resistance to Sunflower Mosaic Virus, resistance to nematodes, resistance to Tobacco Mosaic Virus, resistance to *Papaya* Ringspot Virus, resistance to Zucchini Yellow Mosaic virus, and resistance to *Fusarium* Wilt. In yet another embodiment, the "desirable trait" or "desirable traits" are selected from the group consisting of: fruit size, fruit shape, fruit color, fruit taste, the shelf life of fruit, resistance to Sunflower scab, resistance to Powdery mildew, resistance to Target spot, and resistance to Sunflower mosaic Virus. In still another embodiment the "desirable trait" or "desirable traits" are selected from the group consisting of: fruit size, fruit shape, fruit color, fruit quality acceptable to market, and the shelf life of fruit.

In another embodiment, the invention provides a *Verticillium* wilt resistant sunflower plant, comprising at least a first introgressed sunflower chromosomal region conferring resistance to *Verticillium* wilt, wherein the region is selected from the group consisting of: a *Verticillium* wilt resistance contributing QTL region found on chromosome 10, and a *Verticillium* wilt resistance contributing QTL region found on chromosome 11; further wherein the QTL maps to a position between the sequence represented by SNP marker DHAG001106 and SNP marker DHAI006271, which map to approximately 0 cM and 54.7 cM on the genetic map of the linkage group termed sunflower chromosome 10; wherein the QTL maps to a position between the sequence represented by SNP marker DHAI005760 and SNP marker DHAI006271 which map to approximately 46.5 cM and 54.7 cM on the genetic map of the linkage group termed sunflower chromosome 10; wherein the QTL maps to a position between the sequence represented by SNP marker DHAI000041 and SNP marker DHAI006271 which map to approximately 47.2 cM and 54.7 cM on the genetic map of the linkage group termed sunflower chromosome 10; wherein the QTL maps to a position tightly linked to the sequence represented by SNP marker DHAG000460 which maps to approximately 8.8 cM on the genetic map of the linkage group termed sunflower chromosome 10, or wherein the QTL maps to a position tightly linked to the sequence represented by SNP marker DHAI007648 which maps to approximately 85.4 cM on the genetic map of the linkage group termed sunflower chromosome 11.

In another embodiment, the invention provides a *Verticillium* wilt resistant sunflower plant having a first introgressed sunflower chromosome, wherein the first introgressed sunflower chromosomal region conferring resistance to *Verticillium* wilt comprises an allele present in CN8816R.

In another embodiment, the invention provides a *Verticillium* wilt resistant sunflower plant, comprising the QTL region found on chromosome 10, wherein the QTL is introgressed from CN8816R.

In another embodiment, the invention provides a *Verticillium* wilt resistant sunflower plant further defined as comprising an allele from CN8816R at one or more of markers DHAI006271, DHAI000041, DHAI005760, DHAG001106, and DHAG000460.

In another embodiment, the invention provides a *Verticillium* wilt resistant sunflower plant comprising the QTL region found on chromosome 11, wherein the QTL is introgressed from CN8816R.

In another embodiment, the invention provides a *Verticillium* wilt resistant sunflower plant further defined as comprising an allele from CN8816R at marker DHAI1007648.

In other aspects of the invention, the plants bearing one or more desirable traits in addition to *Verticillium* wilt resistance display a greater than 10%, or a greater than 30%, or a greater than 60%, or a greater than 80% reduction in foliar symptoms of chlorotic and/or necrotic lesions relative to a non-resistant control plant upon inoculation or infection with *Verticillium* wilt. Another aspect of the present invention is directed to a method of producing a *Verticillium* wilt resistant sunflower plant comprising: crossing a sunflower line having *Verticillium* wilt resistance with a second plant lacking *Verticillium* wilt resistance but capable of donating one or more of the aforementioned desirable traits.

EXAMPLES

Example 1: Mapping Populations

Two recombinant inbred lines (RILs) mapping populations based on F3 and F4 generations were developed for a cross between CN8861R and ONN120R. The mapping populations were segregating for the *Verticillium* wilt resistance trait. The populations were grown in the *Verticillium* wilt inoculation field at the Sunflower Breeding Station, Venado Tuerto, Argentina, using a randomized field block design layout. The F1's were developed by crossing the CN8861R (resistant line)×ONN120R (susceptible line) and were advanced to F3 and F4 generations by single seed descent.

Example 2: Phenotyping the Mapping Population

The F3 and F4 families were planted in rows of 15 plants, each derived from individual F2 and F3 plants. In total, 272 and 260 plants rows were grown for the F3 and F4 populations, respectively. Disease phenotyping was based on the natural field inoculation, as the *Verticillium* wilt inoculation field provided a good source of soil borne fungal pathogen *Verticillium dahliae*, the causative agent of this disease, and presented significant disease pressure. Each population was scored for the disease symptoms present on leaves and stems. Leaf symptoms were scored on a scale of 0-4 (0 being resistant and 4 highly susceptible) and were less informative due to similar symptoms for other sunflower diseases. Stem symptoms, which are more definitive for the disease, were scored during the later growth stage after the plants were completely matured and stalks were dried and brown. Individual plants in each row were scored either resistant or susceptible based on the observation of the disease symptoms after splitting open the stem vertically.

For quantitative disease ratings, phenotypic scores for each plant row representing an individual F2 or F3 derived families was calculated as the number of resistant plants in each row (family)/total number of plants in the row.

Example 3: DNA Extraction

Tissue samples were collected from F2 plants and also a single plant from each F4 row for DNA extraction and genotyping with markers. Genomic DNA was extracted from the leaf tissue of the mapping populations and their parental lines on the BioCel 1800 robotic platform (Agilent Technologies, Santa Clara, Calif.) using the Qiagen MagAttract protocol (Qiagen, Valencia, Calif.). The resulting DNA was diluted 1:20 for genotyping.

Example 4: Molecular Markers and Genotyping

The parental lines were genotyped with 270 KASPar™ (KBiosciences, Hoddesdon, Hertfordshire, UK) single nucleotide polymorphism (SNP) markers interspersed throughout the genome in order to identify polymorphic markers. ONV120R a near isogenic line (NIL) to ONN120R, but with *Verticillium* wilt resistance, was developed by backcrossing ONN120R (susceptible line) to Paraiso 20 (resistant source) and was genotyped along with the mapping population. F2 plant samples were genotyped with 95 polymorphic KASPar™ SNP markers. After removing markers and samples that failed during genotyping or were non-informative, the final dataset had 262 individuals and 50 markers. In order to increase the marker coverage an additional 800 KASPar™ SNP markers were developed and parental lines were genotyped to identify polymorphic markers. The F4 population was genotyped with 188 polymorphic KASPar™ SNP markers. Polymorphic markers were selected to represent all 17 linkage groups (LG) of the sunflower genome.

SNP genotyping was performed on each line using the KASPar™ SNP assays following the protocol described below: a volume of 2 µl DNA diluted 1:20 from MagAttract extracted DNA was dispensed into PCR plates. The plates were centrifuged for 1 minute at 5000 rpm and dried for 2 hours at 65° C. The KASP reaction mix was prepared using IX 1536 formula KASP reaction mix (KBiosciences, Hoddesdon, Hertfordshire, UK). A 1.3 µl volume of reaction mix was added to the PCR plates. Plates were laser-sealed with an optically clear permanent seal and were centrifuged for 1 minute at 5000 rpm. Thermal cycling was completed using the touchdown KASP PCR program in the Hydrocycler water bath thermal cycler (KBiosciences, Hoddesdon, Hertfordshire, UK) with the following conditions: initial denaturation and hot-start enzyme activation at 94° C. for 15 minutes followed by 10 cycles of denaturation at 94° C. for 20 seconds and touchdown over 65-57° C. for 60 seconds (dropping 0.8° C. per cycle). This was followed by 29 cycles of denaturation at 94° C. for 20 seconds and 57° C. annealing for 60 seconds. Following PCR, the plates were centrifuged at 5000 rpm for 1 minute and the resulting products were analyzed using the PHERAStar® Spectrofluorometer (BMG LabTech, Cary, N.C.) employing FAM and VIC dye chemistries to distinguish between genotypes. The data was subsequently scored using the KlusterCaller application within the Kraken Laboratory Information Management System (KBiosciences, Hoddesdon, Hertfordshire, UK). In Kraken, the FAM and VIC data are plotted on the x- and y-axes, respectively. Genotypes can then be determined according to sample clusters (FIG. 1).

Example 5: Statistical Analysis

A linkage map was constructed using the JoinMap® 4 (Van Ooijen, 2006) software program. Map order was determined using the regression mapping algorithm with a minimum logarithm-of odds (LOD) threshold of 3.0. Subsequently, permutation tests to determine the significance threshold for LOD score and interval mapping (IM) and multiple-QTL models (MQM) mapping were performed using the MapQTL® 5 (Van Ooijen, 2004) software program.

Figure 2:
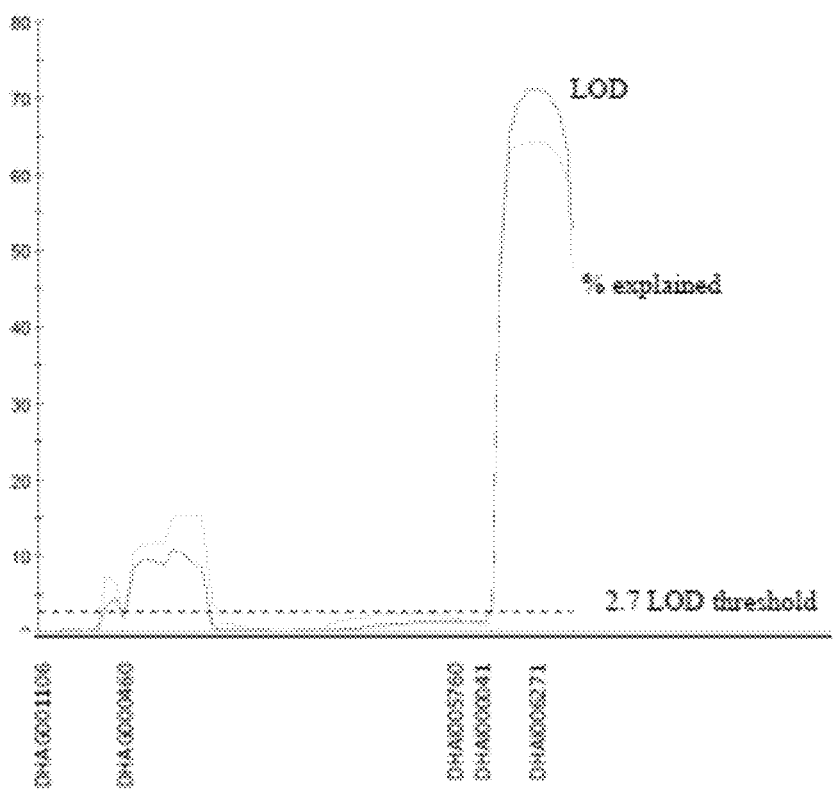
FIG. 2 depicts QTL intervals for the major and minor QTLs on chromosome 10. The location (X-axis) and the significance (LOD score on Y-axis) of the QTLs identified are shown.
Figure 3:
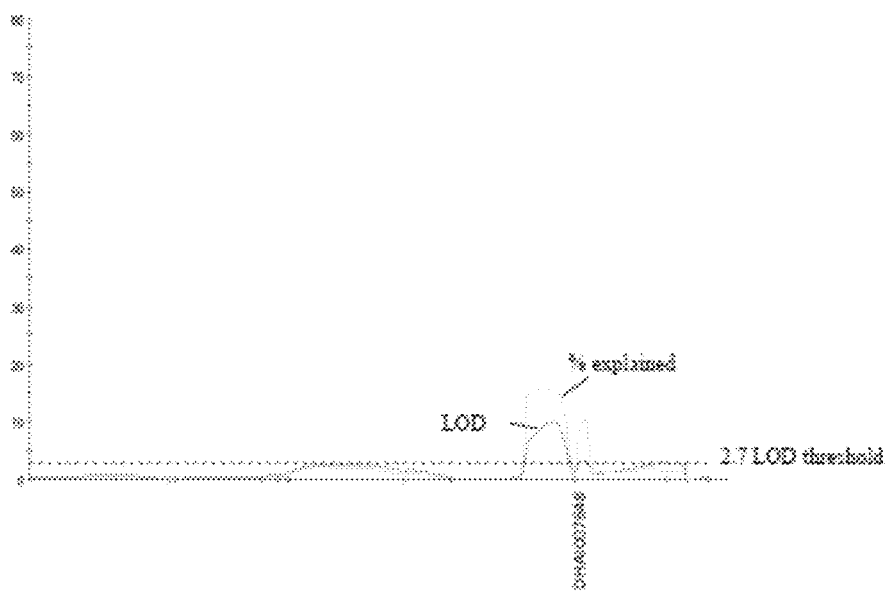
FIG. 3 depicts QTL interval for the minor QTL on chromosome 11. The location (X-axis) and the significance (LOD score on Y-axis) of the QTL identified are shown.

The interval mapping results showed that a single major QTL was located on chromosome 10 in the interval between markers DHAI005760 and DHAI006271, which are separated by approximately 8 cM (FIG. 2). The QTL explains 65% of the variation and has a logarithmic of odds (LOD) score of approximately 72. Two minor QTL were also identified on chromosomes 10 (FIG. 2) and 11 (FIG. 3), each explaining approximately 15% of the variation. The SNP marker DHAG000460 is located in the interval of the minor QTL on chromosome 10 (FIG. 2). The SNP marker DHAI007648 is located in the interval of the minor QTL on chromosome 11 (FIG. 3). Table 2 provides the list of markers either flanking or within the major and minor QTL intervals as well as their sequence and the donor, or resistant, allele for each marker.

TABLE 2

Sequences of the SNP markers located either flanking or within the major and minor QTL on chromosome 10 and 11. Donor alleles are from the *Verticillium* resistant parent, CN8861R.

| Markers | Chromosome | SNP | Donor Allele | SEQ ID NO |
| --- | --- | --- | --- | --- |
| DHAI006271 | 10 | T/C | TT | 1 |
| DHAI000041 | 10 | T/G | GG | 2 |
| DHAI005760 | 10 | A/T | AA | 3 |
| DHAG000460 | 10 | A/C | CC | 4 |
| DHAI007648 | 11 | A/C | CC | 5 |
| DHAG001106 | 10 | A/T | TT | 6 |
| DHAG0000083 | 11 | T/C | CC | 7 |

What is claimed is:

1. A method of identifying a sunflower plant that displays resistance to *Verticillium dahlia* wilt, the method comprising the steps of: a) genotyping a population of sunflower plants, from a segregating population derived from sunflower variety CN8861R, with at least one sunflower genomic nucleic acid marker associated with an allele for *Verticillium dahlia* wilt resistance, wherein said allele comprises at least a first genetic marker genetically linked to a QTL that confers resistance to *Verticillium dahlia* wilt; b) selecting at least a first sunflower plant comprising the genetic marker and the QTL that confers resistance to *Verticillium dahlia* wilt; wherein the QTL maps to a position between the sequence represented by SNP marker DHAI005760 and SNP marker DHAI006271 which map to approximately 46.5 cM and 54.7 cM on the genetic map of the linkage group termed sunflower chromosome 10, and c) crossing the sunflower plant selected in step (b) with another sunflower plant; wherein selecting the first sunflower plant further comprises selecting the plant based on the presence of a plurality of genetic markers that map to a position between the sequence represented by SNP marker DHAI005760 and SNP marker DHAI006271 which map to approximately 46.5 cM and 54.7 cM on the genetic map of the linkage group termed sunflower chromosome 10, and wherein the genetic markers are selected from the group consisting of markers DHAI006271, DHAI000041, and DHAI005760, comprising a single nucleotide polymorphism of one of SEQ ID NOs: 1-3.

2. A method of identifying a sunflower plant that displays resistance to *Verticillium dahlia* wilt, the method comprising the steps of: a) genotyping a population of sunflower plants, from a segregating population derived from sunflower variety CN8861R, with at least one sunflower genomic nucleic acid marker associated with an allele for *Verticillium dahlia* wilt resistance, wherein said allele comprises least a first genetic marker genetically linked to a QTL that confers resistance to *Verticillium dahlia* wilt; b) selecting at least a first sunflower plant comprising the genetic marker and the QTL that confers resistance to *Verticillium dahlia* wilt; wherein the QTL maps to a position between the sequence represented by SNP marker DHAI005760 and SNP marker DHAI006271 which map to approximately 46.5 cM and 54.7 cM on the genetic map of the linkage group termed sunflower chromosome 10; and c) crossing the sunflower plant selected in step (b) with another sunflower plant; wherein the genetic marker is DHAI005760, DHAI000041, or DHAI006271.

* * * * *

SEQUENCE LISTING

```
<160> NUMBER OF SEQ ID NOS: 7

<210> SEQ ID NO 1
<211> LENGTH: 229
<212> TYPE: DNA
<213> ORGANISM: Helianthus annuus

<400> SEQUENCE: 1 ataatttta  aattaaaggt  ttaaaacttg  cattatttac  acgtttcaaa  tataaatgat    60
taaaacatta  tgttatgttt  attcgttaca  taattgtaga  gttaattatt  aaatattatt   120
tggagctaag  cttatagtaa  aayaacttat  tgggttcatt  tgtaacaatg  tgaacatgtg   180
acaactaatt  tgttattaac  ttaatttcca  ttactcccca  acatagacc                229

<210> SEQ ID NO 2
<211> LENGTH: 120
<212> TYPE: DNA
<213> ORGANISM: Helianthus annuus
<220> FEATURE:
<221> NAME/KEY: misc_feature
<222> LOCATION: (98)..(98)
<223> OTHER INFORMATION: n is a, t, c, or g
<220> FEATURE:
<221> NAME/KEY: misc_feature
<222> LOCATION: (118)..(118)
<223> OTHER INFORMATION: n is a, t, c, or g

<400> SEQUENCE: 2
agaaatacgg  acacatgaat  gctgcacaaa  gctgaacagg  ttttgtgctc  tattttttct    60
ktagatcttt  cattggaccg  tcctatttaa  gaacgatnac  ttgtatgtga  tgaaaganga   120

<210> SEQ ID NO 3
<211> LENGTH: 120
<212> TYPE: DNA
<213> ORGANISM: Helianthus annuus

<400> SEQUENCE: 3
gtatctgaag  caacttcaaa  tgcaagtaca  gatgatgtcc  atgggataca  acatggttcc    60
```

```
watgatgttc cccggtgtcc aacgatacat gccggcgatt gctcctttgg gtatgggaat      120

<210> SEQ ID NO 4
<211> LENGTH: 119
<212> TYPE: DNA
<213> ORGANISM: Helianthus annuus
<220> FEATURE:
<221> NAME/KEY: misc_feature
<222> LOCATION: (118)..(118)
<223> OTHER INFORMATION: n is a, t, c, or g

<400> SEQUENCE: 4
tccggtttct tccatgggct tcaccgttcc aggtgtggat attatgtcac atgtggatgm       60
ggatctgaag aagattgcta atcgggttgt ggaaaaggcg aaggagcttt gtgtttcna      119

<210> SEQ ID NO 5
<211> LENGTH: 249
<212> TYPE: DNA
<213> ORGANISM: Helianthus annuus

<400> SEQUENCE: 5
tttataacgc gtgtatacac cgacgaatga taagtttgtt cgactgattt gtatcttaag       60
cttattacct ccaattagat taacactttc aaggccgact tctgaaccat tcaagatccc      120
aaggcaggcg ttaccgtatt tctgtacmaa catatgcaga tgttaaacaa cattgtgaat      180
aaaagaactg ttttagtttt ctcatgacat cttacactaa tgatgagata tgcttcgggg      240
tccatctga                                                              249

<210> SEQ ID NO 6
<211> LENGTH: 120
<212> TYPE: DNA
<213> ORGANISM: Helianthus annuus
<220> FEATURE:
<221> NAME/KEY: misc_feature
<222> LOCATION: (13)..(13)
<223> OTHER INFORMATION: n is a, t, c, or g
<220> FEATURE:
<221> NAME/KEY: misc_feature
<222> LOCATION: (20)..(20)
<223> OTHER INFORMATION: n is a, t, c, or g

<400> SEQUENCE: 6
caccaccacc gcngtraagn ccatggccgg cggcggactc tactccgctc agcaatttga       60
wcttacccca caaaacgtcg acaccgttct cgatgacgtc agaccctacc taattgccga      120

<210> SEQ ID NO 7
<211> LENGTH: 120
<212> TYPE: DNA
<213> ORGANISM: Helianthus annuus
<220> FEATURE:
<221> NAME/KEY: misc_feature
<222> LOCATION: (32)..(32)
<223> OTHER INFORMATION: n is a, t, c, or g

<400> SEQUENCE: 7
taaggaatat agacagaagg tggaaaccga gntgtctaac atttgcaatg atatcatgac       60
ygtgattgat gagcatctga ttccatcttc ctctgctgga gaatctactg ttttctacta      120
```